United States Patent [19]

Bragg

[11] 4,005,722
[45] Feb. 1, 1977

[54] TOOL FOR FLOSSING TEETH UNDER A PERMANENT BRIDGE

[76] Inventor: Kenneth R. Bragg, 635 Pasco De La Playd, Redondo Beach, Calif. 90274

[22] Filed: Apr. 8, 1976

[21] Appl. No.: 674,894

[52] U.S. Cl. .............................................. 132/92 R
[51] Int. Cl.² ........................................ A61C 15/00
[58] Field of Search ........................... 132/92 R, 91

[56] References Cited

UNITED STATES PATENTS

| 3,696,821 | 10/1972 | Adams | 132/91 |
| 3,799,177 | 3/1974 | Bragg | 132/92 R |
| 3,901,251 | 8/1975 | Johnston | 132/91 |

*Primary Examiner*—G.E. McNeill
*Attorney, Agent, or Firm*—John N. Wolfram

[57] ABSTRACT

A dental flossing tool comprising two tool members. One member supports a strand of floss between two closely spaced portions and the other member has a laterally projecting wire with a hook shape at the free end thereof. The wire is insertable between two teeth of a person and hooks the strand floss between the tips of the other member so that the floss can be pulled between the teeth by withdrawal of the wire from between the teeth. Upon such withdrawal, the two members can then be manipulated for flossing the two teeth. The invention has particular application for flossing the supporting teeth of a permanent bridge.

18 Claims, 10 Drawing Figures

TOOL FOR FLOSSING TEETH UNDER A PERMANENT BRIDGE

BACKGROUND OF THE INVENTION

When using dental floss for flossing a person's teeth, it is the common practice to insert the floss between two adjacent teeth by supporting and pulling taut a floss strand either with the person's fingers or with a tool such as disclosed in my U. S. Letters Patent 3,799,177 and then sliding the floss between the teeth from the top edge thereof. However, when a person has a permanent bridge it is not possible to slide the floss between the supporting teeth. Also, in some instances a person may have two teeth that are too close together to pemit vertical sliding of the floss in and out from between the teeth.

SUMMARY OF THE INVENTION

The present invention provides a flossing tool for use in flossing between supporting teeth for a bridge or between two teeth that are too close together to permit the floss to be inserted by sliding it from the top of the teeth toward the gum.

The invention utilizes two basic members. One member has two closely spaced tip portions and means to support the floss so that it extends between the two tips. The other member has a tip portion which a wire projects laterally. The wire has a hook at its free end.

To use the tool, a person places the one member so that the two tip portions are on one side of the two teeth to be cleaned. The other member is then manipulated so that the wire is inserted sidewards between the two teeth from the other side thereof to hook the floss between the two tips of the other member. The wire is then withdrawn from between the teeth, pulling the floss into the space between the teeth. The two tools are then manipulated for flossing the adjacent sides of the two teeth. Upon completion, the one tool is maneuvered to release the floss from the hook and the floss is then pulled from between the teeth by the member that carries the floss.

DETAIL DESCRIPTION

Figure 2:
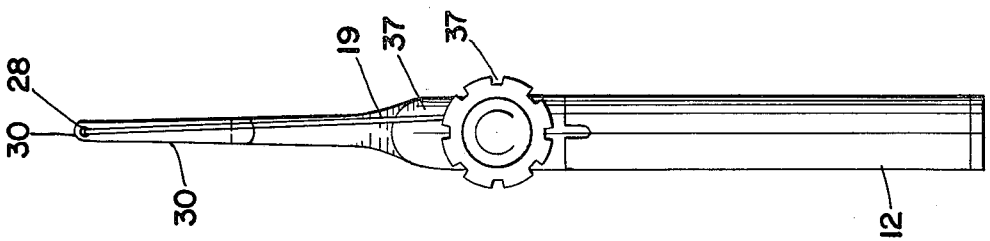
FIG. 2 is a side view of the member of FIG. 1.
Figure 1:
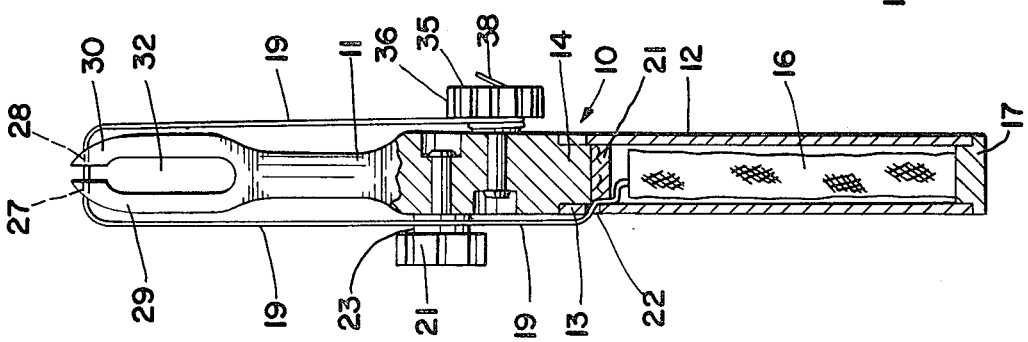
FIG. 1 is a view partly in section of one form of the tool member that carries the floss.

The tool member 10 as shown in FIGS. 1 and 2 comprises a unitary assembly in which there is a body member 11 to which a tube 12 is press fitted at 13 to an extension 14 of body 11. Tube 12 serves as a handle and also houses a coiled supply of floss 16 which is retained therein by a cap 17 that closes the end of the tube. A floss strand 19 from the supply coil 16 passes along the periphery of a fibrous pad 21 that squeezes the strand against the inside surface of tube 12 before it passes through a side opening 22 to be wound with several turns on a cylindrical surface 23 of a rotatable spool 24 that is mounted on body 11. From spool 24 the floss strand is threaded through openings 27, 28 in a pair of slender tip portions 29, 30 of body 11 that are closely spaced so as to form an opening 32 therebetween. From tip 30 the floss is lead to a cylindrical portion 34 of a collecting spool 35 which has a nob 36 thereon. The floss is wound with several turns on portion 34 and is then lead along one of a series of axial grooves 37 in nob 36 to a cutter member 38 mounted on spool 35.

Figure 3:
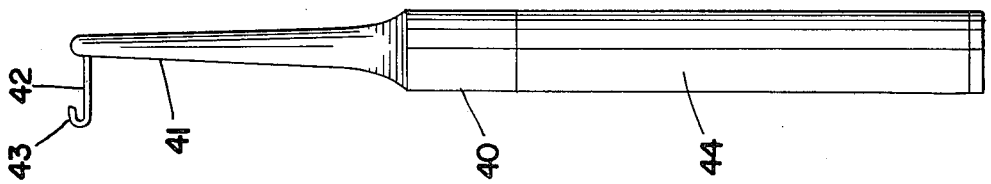
FIG. 3 is a side view of the tool member that carries the wire hook.

The tool includes another member 40, shown in FIG. 3, which has a slender top portion 41 and a handle 44. Extending laterally from tip 41 is a wire 42 having a hood 43 at its free end that is in the form of a small loop having a turn that is more than 180° and preferably not more than 270° so that the loop can be passed between a person's teeth without the free end of the wire scratching or cutting the gum.

Figure 8:
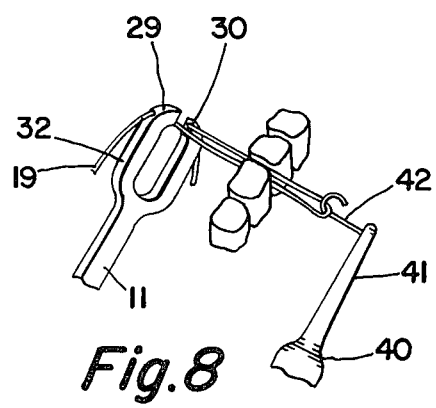
FIG. 8 is a view showing how the tool is used.

To use the tool between teeth that are too close together to permit the floss to be inserted from the top of the teeth toward the gum, member 11 is placed on one side of the two teeth that are to be cleaned, as shown in FIG. 8. Tool member 40 is then brought into position on the other side of the two teeth so that wire 42 can be inserted between the two teeth and into the opening 32 of tool member 11 so that the latter can be moved to cause the floss strand portion extending between the two tips 29 and 30 to be caught by hook 43. Withdrawal spool 24 is then turned to withdraw additional floss from tube 12. Tool member 40 is then manipulated to withdraw wire 42 from between the teeth and pulling with it a loop of floss strand. The two tool members 11 and 40 may then be manipulated for moving this loop of strand floss against the adjacent sides of the two teeth for cleaning the same. When the two teeth are cleaned, tool member 40 is manipulated to release hood 43 from the loop of floss and the latter is then withdrawn from between the two teeth either by simply pulling it with tool member 11 or by rotation of spool 35 for winding the floss strand on cylindrical portion 34.

In a similar manner the tool may be used to floss between two teeth for which access therebetween cannot be achieved from the top of the teeth because of an overlaying permanent bridge.

In the form of invention shown in FIGS. 4–7, the tool member that supports the floss is in the form of two separate sections 50–51. Section 50 has a tube 12 thereon that serves both as a handle and as a container for a supply of floss, as in FIG. 1. Section 50 also has a withdrawal spool 24 thereon corresponding to spool 24 of FIG. 1 and it has a tip 53 for supporting the floss strand 19. Near spool 24 section 50 has a recess 55 with an undercut surface 56 and at the bottom of tube 12 there is a closure cap 57 having a recess 58. Section 51 also has a tip 61 for supporting the strand of floss and there is a withdrawal spool 35 corresponding to spool 35 of FIG. 1. Section 51 has a tubular handle 12 closed at its bottom end by a cap 63. Near spool 35 section 51 has a laterally extending prong 64 with an undercut surface 65. Cap 63 likewise has a laterally extending prong 66 with an abutment surface 67. Sections 50, 51 and caps 57, 63 are made of a plastic material such as polycarbonate and prongs 64 and 66 have enough flexibility so that they can be deflected slightly. Further-more, the polycarbonate material has sufficient resiliency so that upon release of the deflected prongs they will spring back to their original position.

Figure 5:
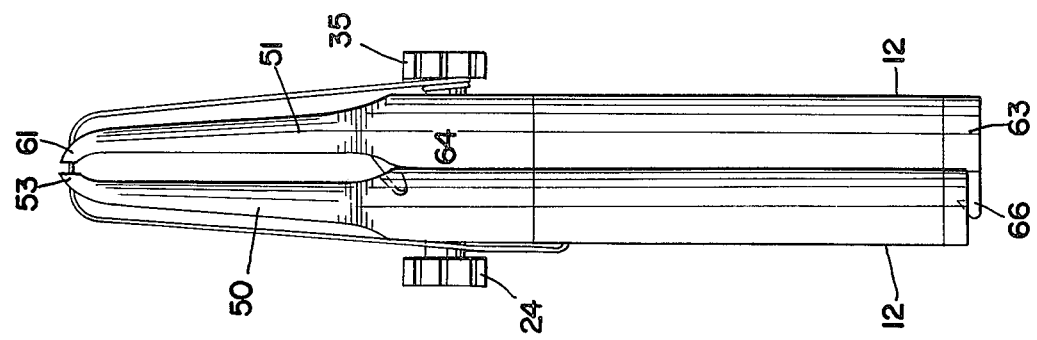
FIG. 5 is a view of a tool member of FIG. 4 in which the separable sections are connected to each other.
Figure 4:
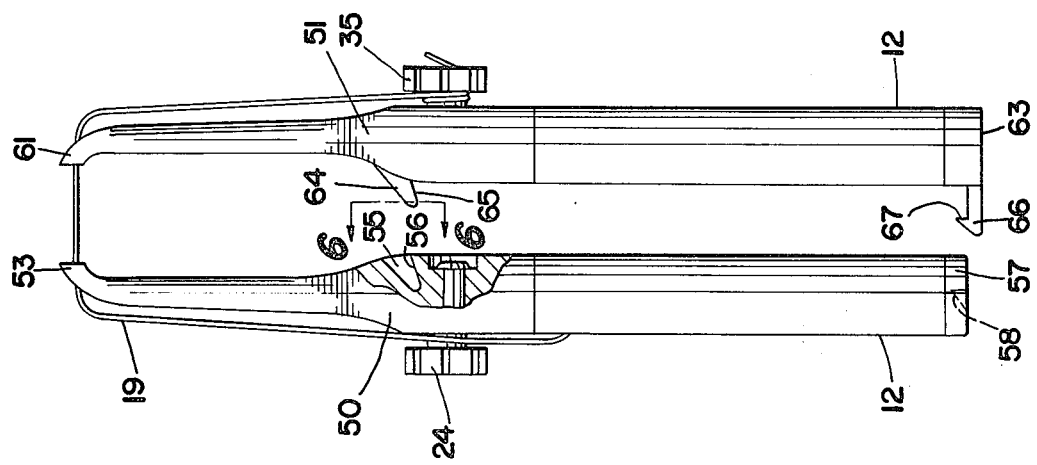
FIG. 4 shows the tool member that carries the floss wherein such tool member is comprised of two separate sections connectable to each other.

The tool sections 50, 51 of FIG. 4 comprise a complete tool for normal flossing of the teeth. A similar tool, but without recesses 55, 58 and prongs 64, 66 is described in more detail in my co-pending patent application Ser. No. 674,889 filed May 27, 1976. However, by utilizing prongs 64 and 66 to fasten section 51 to section 50, as shown in FIG. 5, the tool of FIGS. 4 and 5 can be used in conjunction with the tool member 40 of FIG. 3 to draw floss between two teeth under a bridge in the same manner as described in connection with the tool member of FIGS. 1 and 2.

Figure 6:
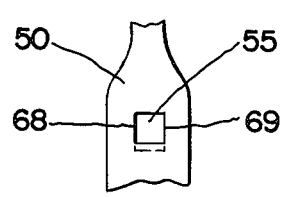
FIG. 6 is a view at 6—6 of FIG. 4
Figure 7:
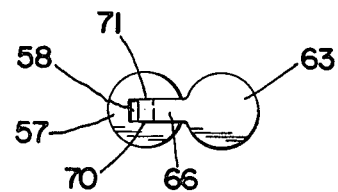
FIG. 7 is an end view of FIG. 5.

As shown in FIGS. 6 and 7, recesses 55 and 58 each have respective sidewalls 68, 69 and 70, 71 to prevent the respective prongs 64, 66 to move sidewardly out of such recesses.

Figure 9:
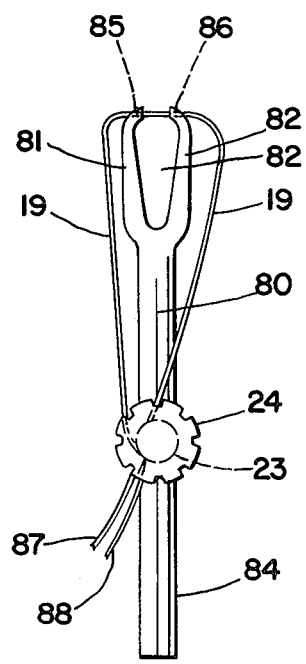
FIG. 9 is a plan view of a modified form of the invention.
Figure 10:
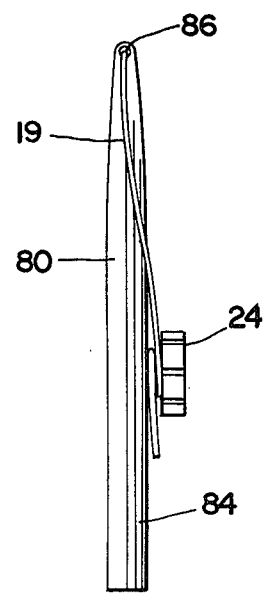
FIG. 10 is a side view of FIG. 9.

In the form of the tool shown in FIG. 9, member 80 has a pair of spaced tips 81, 82 with an adjacent opening 83 and it also carries a collecting spool 24 of FIG. 1 and has a cylindrical section 23. In this case, member 80 does not necessarily carry a supply of floss in its handle portion 84.

To use member 80 in conjunction with member 40, a section of floss 19 is cut from a supply and threaded through openings 85, 86 in tips 81 and 82. The two ends 87, 88 of the strand are then brought together and the portion of the floss near these ends is wrapped in one direction about spool cylindrical surface 23 until the floss is taut between tips 81, 82 and spool 24.

Member 80 is then positioned with tips 85, 86 near one side of two adjacent teeth and member 40 is manipulated to insert wire 42 between these teeth from the other side thereof whereby the floss strand between tips 85, 86 can be hooked by hook 43. Spool 24 is then rotated in a direction for loosening the floss and a loop of the floss is pulled between the teeth by use of hook 43. The two members 80 and 40 are then used to perform the flossing operation after which the floss is released from the hook and withdrawn from between the teeth.

In a further modification of the tools illustrated in FIGS. 1 through 7, spool 24 may be omitted and fibrous pad 21 is fitted into tube 12 sufficiently tight to put enough frictional drag upon the floss strand 19 to prevent withdrawal of floss from within tube 12 during normal use of the tool within a person's mouth but yet permit floss to be withdrawn by a firm pull thereon by rotation of collecting spool 35 and/or by hook 43.

I claim:

1. A flossing tool comprising in combination a first member providing first and second spaced tips, means on the tips for supporting a strand of floss therebetween, a second member having a third tip with a wire extending therefrom, said wire having a hook, said wire being insertable between two adjacent teeth of a person whereby when the tips of the first member are placed on one side of said two teeth the wire may be inserted between said teeth from the other side thereof so as to hook the floss between the pair of tips so that upon withdrawal of the wire from between said teeth the floss is pulled between said teeth where it may be manipulated by the two members for cleaning the adjacent surfaces of said teeth.

2. The tool of claim 1 in which said first member comprises a single unitary structure.

3. The tool of claim 1 in which said first and second tips are carried by said first member in fixed relation to each other.

4. The tool of claim 1 in which said supporting means on said first and second tips is at a fixed location and there is an opening through said member adjacent said first and second tips for receiving said hook.

5. The tool of claim 1 in which said first member has a means thereon for securing the floss to the member.

6. The tool of claim 1 in which said securing means is operable for making the floss loose or tight between said first and second tips.

7. The tool of claim 1 in which said first member has means thereon for storing a supply of floss, means on one side of said first and second tips for withdrawing floss from the storing means, and means on the other side of said first and second tips for collecting the floss.

8. The tool of claim 1 in which said first member comprises first and second independent sections that respectively carry the first and second tips, and means for attaching the sections to each other.

9. The tool of claim 8 in which said atttaching means includes at least one flexible prong on one section that may be snapped over an abutment surface on the other section.

10. The tool of claim 8 in which said attaching means includes releasable interlocking means.

11. The tool of claim 9 in which said abutment surface is one wall of a recess that has a pair of side walls to prevent sideward movement of the prong from the recess.

12. The tool of claim 1 in which said hook comprises a turn in the wire of more than 180°.

13. The tool of claim 12 in which the turn is not greater than 270°.

14. The tool of claim 8 in which said attaching means comprises first and second spaced pairs of cooperating holding means.

15. The tool of claim 14 in which at least one of said cooperating holding means comprises a flexible prong on one of the sections having a holding shoulder engageable with a holding shoulder on the other section.

16. The tool of claim 1 in which said second member is elongated and said wire projects substantially at right angles to a lengthwise axis of the second member.

17. The tool of claim 6 in which said securing means comprises a projection on the first member around which portions of the floss strand from opposite sides of said first and second tips may be wrapped.

18. The tool of claim 17 in which said securing means comprises a spool mounted on the first member and which may be rotated for tightening or loosening the floss at said first and second tips when said portions are wound upon the spool in the same direction.

* * * * *